US00PP34820P3

(12) United States Plant Patent
Brown

(10) Patent No.: US PP34,820 P3
(45) Date of Patent: Dec. 13, 2022

(54) ***CALLISTEMON* PLANT NAMED 'CNU15'**

(50) Latin Name: *Callistemon citrinus*
Varietal Denomination: CNU15

(71) Applicant: Nuflora International Pty Ltd, Macquarie Fields (AU)

(72) Inventor: Graham Brown, Bowral (AU)

(73) Assignee: Nuflora International Pty Ltd, Macquarie Fields (AU)

( * ) Notice: Subject to any disclaimer, the term of this patent is extended or adjusted under 35 U.S.C. 154(b) by 0 days.

(21) Appl. No.: 17/803,224

(22) Filed: Mar. 21, 2022

(65) Prior Publication Data

US 2022/0304205 P1 Sep. 22, 2022

Related U.S. Application Data

(60) Provisional application No. 63/163,815, filed on Mar. 20, 2021.

(51) Int. Cl.
*A01H 5/02* (2018.01)
*A01H 6/00* (2018.01)

(52) U.S. Cl.
USPC ..... Plt./226
CPC ..... *A01H 6/00* (2018.05); *A01H 5/02* (2013.01)

(58) Field of Classification Search
USPC ..... Plt./226
CPC ..... A01H 5/02; A01H 5/00
See application file for complete search history.

(56) References Cited

PUBLICATIONS https://australianplantspecialists.com.au/wp-content/uploads/2021/05/Full-range-2020.21.pdf; May 2021; pp. 1-12.*

* cited by examiner

*Primary Examiner* — Kent L Bell
(74) *Attorney, Agent, or Firm* — Samuel R. McCoy, Jr.

(57) ABSTRACT

A new and distinct variety of *Callistemon* plant named 'CNU15' which is characterized by the combination of a compact growth habit, cylindrical inflorescences comprised of an abundance of light pink flowers, and the stability of all characteristics from generation to generation.

2 Drawing Sheets

Latin name of the genus and species: The Latin name of the genus and species of the novel variety disclosed herein is *Callistemon citrinus.*

Variety denomination: The inventive variety of *Callistemon* disclosed herein has been given the variety denomination 'CNU15'.

BACKGROUND OF THE INVENTION

Parentage: 'CNU15' is the result of a controlled cross-pollination breeding program carried out by the inventor at a commercial plant breeding facility in Cobbitty, New South Wales, Australia in October of 2014. The inventor performed a controlled cross-pollination of the seed parent, *Callistemon* 'Hot Pink' (South African Plant Breeder's Rights grant number ZA 20043189) with *Callistemon* 'Mauve Mist' (unpatented), the pollen parent. The resulting seedlings were grown for two years to evaluate for new and distinct characteristics. In October of 2016, the inventor selected the new *Callistemon* plant for its compact growth habit and light pink flowers. This new and distinctive cultivar was given the name 'CNU15'

Asexual Reproduction: Asexual reproduction of 'CNU15', by way of stem cuttings, was first initiated in 2016 in Cobbitty, New South Wales, Australia. Through greater than four subsequent generations of asexual propagation, the unique features of this cultivar have proven to be stable and true to type.

SUMMARY OF THE INVENTION

The cultivar 'CNU15' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'CNU15'. These characteristics in combination distinguish 'CNU15' as a new and distinct *Callistemon* cultivar:

1. *Callistemon* 'CNU15' exhibits a compact growth habit; and
2. *Callistemon* 'CNU15' exhibits cylindrical inflorescences with an abundance of light pink flowers; and
3. *Callistemon* 'CNU15' exhibits flowers with light pink exserted stamens.

BOTANICAL DESCRIPTION OF THE PLANT

Figure 1:
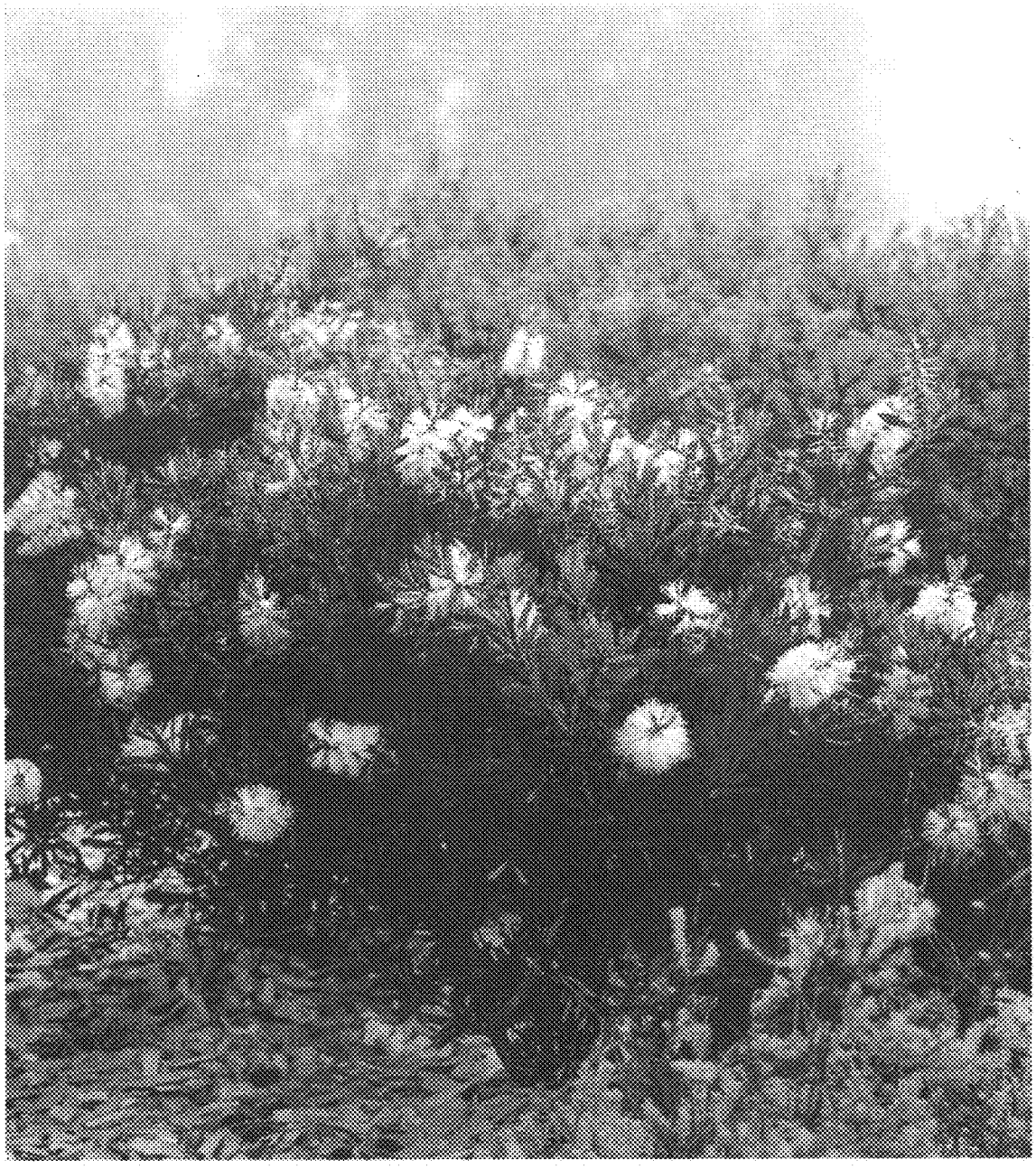
FIG. 1 illustrates, as nearly true as it is reasonably possible to make the same in color photographs of this type, an exemplary plant of 'CNU15'. This plant is approximately 36 months old.
Figure 2:
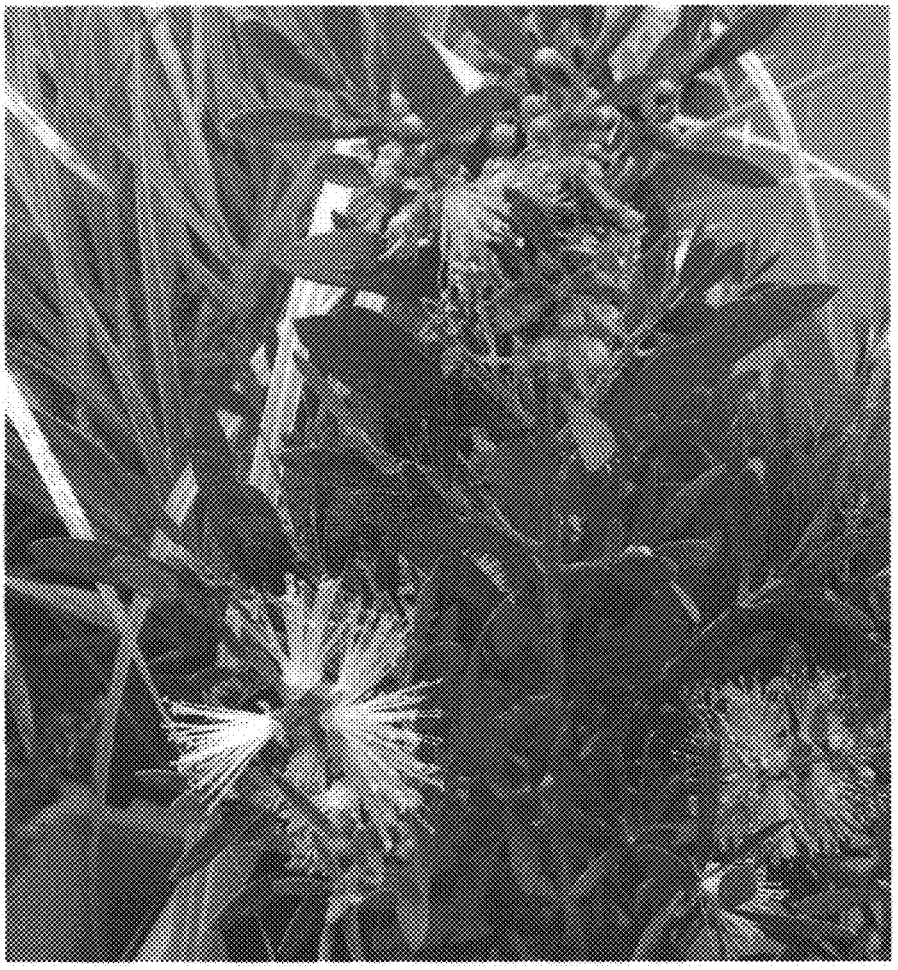
FIG. 2 illustrates, as nearly true as it is reasonably possible to make the same in color photographs of this type, the typical inflorescence of 'CNU15'.

The following observations and measurements were made in May of 2022 and describe a 6-year-old 'CNU15' plant grown in the ground in Clarendon, New South Wales, Australia. The plant was allowed to grow with full sun exposure and maintained with sporadic overhead irrigation during prolonged drought conditions and slow-release granular fertilizer applications. The plant received a light prune, biannually. No pest or disease control measures were utilized in production.

Those skilled in the art will appreciate that certain characteristics will vary with older or, conversely, with younger plants. 'CNU15' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart,* The Royal Horticultural Society, London, 1986 (third edition).

A botanical description of 'CNU15', comparisons with the parents, comparisons with sibling cultivars, and a comparison with the most similar variety of common knowledge are provided below.

General plant description:

*Growth habit.*—Evergreen shrub with a compact, globular growth habit.

*Plant profile.*—Rotund.

*Height.*—120 cm from the soil level to the top of the foliar plane.

*Plant spread.*—120 cm.

*Growth rate.*—Moderately fast.

*Plant vigor.*—Moderately vigorous.

*Propagation type.*—Stem cuttings.

*Time to produce a rooted cutting.*—Approximately 120 days to produce a rooted cutting at approximately 25 degrees Celsius.

*Time to produce a finished plant.*—32 weeks to produce a fully rooted 15 cm container.

*Disease and pest resistance.*—Neither resistance nor susceptibility to typical *Callistemon* pests and diseases has been observed.

*Environmental tolerances.*—Adapt to, at least, USDA Zones 9 through 11; moderate tolerance to rain; moderate to high tolerance to wind; drought tolerant once established.

Root system:

*General.*—Moderately dense and freely branched rooting; roots are moderately fibrous.

*Distribution in the soil profile.*—Shallow to moderately deep.

Stem:

*General branching habit.*—A single main stem, freely branching from the base, with an abundance of lateral branches.

*Quantity of main stems per plant.*—1.

*Diameter of the main stem.*—9.5 cm at soil level.

*Abundance of lateral branches.*—Abundant.

*Length of lateral branches.*—Approximately 74 cm.

*Diameter of lateral branches.*—Approximately 0.9 cm.

*Internode length.*—Approximately 0.3 cm.

*Attitude of lateral branches.*—Outward to upright.

*Aspect.*—Rounded.

*Texture, juvenile.*—Tomentose.

*Texture, mature and oldest wood.*—Glabrous and becoming progressively fissured and furrowed with age, followed by exfoliation of the outer bark in small segments, revealing yet more fissured and furrowed bark beneath.

*Luster.*—Slightly glossy to matte.

*Strength.*—Strong.

*Color, juvenile lateral branches.*—Greyed-purple, nearest to RHS 184D, and becoming progressively suffused with yellow-green, RHS 144D, and later with greyed-orange, nearest to RHS 164C.

*Color, mature lateral branches.*—Greyed-orange, distally, nearest to in between 164C and 164D; nearest to a combination of greyed-white and greyed-green, proximally, RHS 156C and 196D.

*Color, main stem.*—Exfoliating bark is a combination of greyed-green and brown, nearest to RHS 196A, 200A, 200B, and 200D; exposed wood below the exfoliating bark is greyed-orange, nearest to a combination of RHS 164A, 164C, 164D, and 166C.

Foliage:

*Arrangement.*—Whorled.

*Division.*—Simple.

*Attachment.*—Petiolate.

*Attitude.*—Upward and outward.

*Lamina.*—Shape — Nearest to oblanceolate. Aspect — Flat to very slightly carinate; margins occasionally revolute. Dimensions — 5.9 cm long and 1.05 cm wide. Apex — Broad acute with a very short, soft mucronate tip. Base — Cuneate. Margin — Entire; not undulated. Texture of the juvenile foliage, adaxial surface — Tomentose. Texture of the juvenile foliage, abaxial surface — Tomentose. Texture of the mature foliage, adaxial surface — Coriaceous; glabrous. Texture of the mature foliage, abaxial surface — Coriaceous; glabrous. Luster of the juvenile foliage, adaxial surface — Matte. Luster of the juvenile foliage, abaxial surface — Matte. Texture of the mature foliage, adaxial surface — Moderately glossy. Texture of the mature foliage, abaxial surface — Matte to slightly glossy. Color — Juvenile foliage, adaxial surface — Nearest to in between greyed-red and greyed-purple, RHS 182B and 185C. Lamina becomes progressively suffused with green, RHS 137B, with age. Juvenile foliage, abaxial surface — Nearest to in between greyed-red and greyed-purple, RHS 182B and 185C. Lamina becomes progressively suffused with green, RHS 137C, with age. Mature foliage, adaxial surface — Nearest to in between green and yellow-green, RHS 137A and 147A. Mature foliage, abaxial surface — Green, nearest to in between RHS 137B and 137C. Venation — Pattern — Pinnate. Color, adaxial surface — Same as the surrounding foliage; nearest to in between green and yellow-green, RHS 137A and 147A. Color, abaxial surface — Same as the surrounding foliage; green, nearest to in between RHS 137B and 137C.

*Petiole.*—Length — 0.25 cm. Diameter — 0.1 cm at the base. Strength — Strong. Texture, juvenile — Tomentose. Texture, mature — Smooth; glabrous. Luster, juvenile — Matte. Luster, mature — Slightly glossy. Color, adaxial and abaxial surfaces — Juvenile petioles are colored greyed-greyed-purple, nearest to RHS 184D. Mature petioles are yellow-green, nearest to a mixture of RHS 145A and 151B.

*Stipules.*—None observed.

Inflorescence:

*Habit*.—Terminal leafy spikes, borne directly on the lateral branches.

*Natural flowering season*.—Heaviest bloom period is spring, with sporadic flowering through summer and a second larger flush of blooms in autumn, in Zone 9 of the United States.

*Time to flower or response time*.—Approximately 6 months.

*Dimensions*.—Largest inflorescence observed is 6.1 cm long and 5.8 cm in diameter.

*Quantity of flowers per inflorescence*.—36, on the largest observed inflorescence.

*Peduncles*.—None.

Flower buds:

*Shape*.—Broad oblong to obovoid.

*Length*.—6.0 mm.

*Diameter*.—3.5 mm.

*Texture*.—Coriaceous; proximal end at the calyx is tomentose and distal end at the flower petals is glabrous.

*Luster*.—Slightly glossy.

*Color*.—Yellow-green, nearest to in between RHS 144B and 147A; immature sepal lobes are suffused with greyed-purple, nearest to RHS 185B.

Flower:

*Shape, type*.—Rotate, with a single whorl of petals.

*Attachment*.—Sessile.

*Flowering habit*.—Freely flowering.

*Attitude*.—Upright to outward.

*Flower longevity on plant*.—Approximately 7 to 10 days.

*Persistent or self-cleaning*.—Self-cleaning.

*Fragrance*.—Non-fragrant.

*Diameter*.—Diameter of the corolla is 6.75 mm; the width across the exserted stamens at their distal end is 18.0 mm.

*Depth*.—Depth of the corolla, including the stamens, is 24.0 mm.

*Pedicels*.—None; flowers are sessile.

*Calyx*.—Shape — Campanulate with sepal lobes adpressed to the corolla at anthesis. Length — 4.5 mm, including the sepal lobes. Diameter — 3.75 mm, distally, at the sepal lobes. Color of the calyx tube — Yellow-green, nearest to a mixture of RHS 144B and 144C. Sepal lobes — Quantity — 5. Shape — Deltoid. Dimensions — 1.0 mm long and 1.9 mm wide at the base. Apex — Obtuse. Base — Fused to the calyx tube. Margin — Entire. Texture — Tomentose. Luster — Matte. Color — Yellow-green, nearest to a mixture of RHS 144C and 145A, and heavily suffused with greyed-purple, nearest to RHS 185B.

*Petals*.—Quantity — 5. Arrangement — Rotate. Length — 3.25 mm. Width — 2.75 mm. Shape — Near orbicular. Apex — Obtuse. Base — Truncate. Margin — Entire; no undulation. Texture, inner surface — Glabrous; coriaceous. Texture, outer surface — Glabrous; coriaceous. Petal color — When opening, inner surface — Yellow-green, nearest to RHS 145C and suffused with 145A. When opening, outer surface — Yellow-green, nearest to in between 145A and 145B. Fully opened, inner surface — Yellow-green, nearest to RHS 145C and suffused with 145A. Fully opened, lower surface — Yellow-green, nearest to in between 145A and 145B. Petal venation color — No venation is visible.

Reproductive organs:

*Androecium*.—Stamens — Quantity — As many as 45 observed. Anthers — Attachment — Dorsifixed. Shape — Oblong. Dimensions — 0.75 mm long and 0.4 mm wide. Color — Yellow-green, nearest to in between RHS 150A and 151D, and aging to greyed-orange, nearest to a combination of RHS 164D and 165C. Filaments — Length — 17.0 mm, on average. Diameter — 0.25 to 0.30 mm. Color — Light red-purple, nearest to in between RHS 70D and 73B. Amount of Pollen — Moderately abundant. Pollen color — Yellow, nearest to RHS 4A.

*Gynoecium*.—Pistil — Quantity — One. Length — 17.0 mm. Style — Length — 16.0 mm, on average. Diameter — 0.5 mm. Color — Yellow-green, RHS 145D, at the base and becoming darker towards and at the stigma, nearest to in between RHS 145B and 145C. Stigma — Shape — Near globular. Length — 1.0 mm. Diameter — 0.75 cm. Color — Yellow-green, RHS 145A, and lightly suffused with RHS 151D. Ovary position — Inferior.

Seed and fruit: Seeds not observed.

Comparisons With the Parent Plants

Plants of the new cultivar 'CNU15' differ from its seed parent, *Callistemon* 'Hot Pink' (South African Plant Breeder's Rights grant number ZA 20043189), by the characteristics described in Table 1.

TABLE 1

| Characteristic | 'CNU15' | 'Hot Pink' |
|---|---|---|
| General coloration of the stamens. | Light pink. | Red-purple. |

Plants of the new cultivar 'CNU15' may be distinguished from its pollen parent, *Callistemon* 'Mauve Mist' (not patented), by the characteristics described in Table 2.

TABLE 2

| Characteristic | 'CNU15' | 'Mauve Mist' |
|---|---|---|
| General coloration of the stamens. | Light Pink. | Purple. |

Comparison With the Most Similar Variety of Common Knowledge

Plants of the new cultivar 'CNU15' may be distinguished from the most similar known commercial comparator, *Callistemon* 'Angela' (unpatented), by the characteristics described in Table 3.

TABLE 3

| Characteristic | 'CNU15' | 'Angela' |
|---|---|---|
| Plant height. | Shorter than 'Angela'. | Taller than 'CNU15' |

Plants of the new cultivar 'CNU15' may be distinguished from its sibling, *Callistemon citrinus* 'CNU01' (co-pending U.S. Plant patent application Ser. No. 17/803,225), by the characteristics described in Table 4.

TABLE 4

| Characteristic | 'CNU15' | 'CNU0' |
|---|---|---|
| Growth habit. | Compact; globular. | Compact; globular to near columnar. |
| Plant height. | Shorter than 'CNU01'. | Taller than 'CNU15' |
| General coloration of the stamens. | Light Pink. | White. |

Plants of the new cultivar 'CNU15' may be distinguished from its sibling, *Callistemon citrinus* 'CNU06' (co-pending U.S. Plant patent application Ser. No. 17/803,228), by the characteristics described in Table 5.

TABLE 5

| Characteristic | 'CNU15' | 'CNU06' |
|---|---|---|
| Plant size. | Smaller than 'CNU06' | Larger than 'CNU15'. |
| Foliage size. | Smaller than 'CNU06' | Larger than 'CNU15'. |
| Inflorescence size. | Smaller than 'CNU06' | Larger than 'CNU15'. |
| General coloration of the stamens. | Light Pink. | Light Pink. |

Plants of the new cultivar 'CNU15' may be distinguished from its sibling, *Callistemon citrinus* 'CNU07' (co-pending U.S. Plant patent application Ser. No. 17/803,227), by the characteristics described in Table 6.

TABLE 6

| Characteristic | 'CNU15' | 'CNU07' |
|---|---|---|
| Growth habit. | Compact; globular. | Upright; columnar. |
| Plant height. | Shorter than 'CNU07'. | Taller than 'CNU15' |
| General coloration of the stamens. | Light Pink. | White. |

Plants of the new cultivar 'CNU15' may be distinguished from its sibling, *Callistemon citrinus* 'CNU19' (co-pending U.S. Plant patent application Ser. No. 17/803,223), by the characteristics described in Table 7.

TABLE 7

| Characteristic | 'CNU06 | 'CNU19' |
|---|---|---|
| Growth habit. | Compact; globular. | Upright; columnar. |
| Plant size. | Smaller than 'CNU19'. | Larger than 'CNU15' |
| General coloration of the stamens. | Light pink. | Dark pink. |

That which is claimed is:

1. A new and distinct variety of *Callistemon* plant named 'CNU15', substantially as described and illustrated herein.

* * * * *